United States Patent
Faris et al.

(10) Patent No.: US 7,906,343 B2
(45) Date of Patent: Mar. 15, 2011

(54) SURFACE-ENHANCED LANTHANIDE CHELATES

(75) Inventors: Gregory W. Faris, Menlo Park, CA (US); Jeanne P. Haushalter, Los Gatos, CA (US)

(73) Assignee: SRI International, Menlo Park, CA (US)

( * ) Notice: Subject to any disclaimer, the term of this patent is extended or adjusted under 35 U.S.C. 154(b) by 340 days.

(21) Appl. No.: 11/813,468

(22) PCT Filed: Jan. 24, 2006

(86) PCT No.: PCT/US2006/002893
§ 371 (c)(1), (2), (4) Date: Jul. 6, 2007

(87) PCT Pub. No.: WO2007/084141
PCT Pub. Date: Jul. 26, 2007

(65) Prior Publication Data
US 2008/0194044 A1 Aug. 14, 2008

Related U.S. Application Data

(60) Provisional application No. 60/646,902, filed on Jan. 24, 2005.

(51) Int. Cl.
*G01N 33/551* (2006.01)

(52) U.S. Cl. .......... 436/524; 436/518; 436/525; 435/7.1; 435/283.1; 435/287.1; 435/287.2; 422/50; 422/82.05

(58) Field of Classification Search .................. 436/518, 436/524, 525; 435/7.1, 283.1, 287.1, 287.2; 422/50, 82.05
See application file for complete search history.

(56) References Cited

U.S. PATENT DOCUMENTS

| | | | | |
|---|---|---|---|---|
| 4,962,045 | A | * | 10/1990 | Picozza et al. ............... 436/501 |
| 4,978,625 | A | * | 12/1990 | Wagner et al. ............... 436/518 |
| 5,227,474 | A | * | 7/1993 | Johnson et al. ............... 534/558 |
| 7,332,344 | B2 | | 2/2008 | Morgan |
| 2003/0228682 | A1 | * | 12/2003 | Lakowicz et al. .......... 435/287.2 |
| 2006/0147927 | A1 | * | 7/2006 | Geddes et al. .................... 435/6 |

OTHER PUBLICATIONS

Lakowicz et al., Effects of Silver Island Films on the Luminescent Intensity and Decay Times of Lanthanide Chelates, 2002, Jouranl of Fluorescence, vol. 12, pp. 431-437.*

Li et al., Amine reactive forms of a luminescent diethylenetriaminepentaacetic acid chelate of Terbium and Europium: Attachment to DNA and Energy Transfer Measurements, 1997, Bioconjugate Chemistry, vol. 8, pp. 127-132.*

Lakowicz et al., Effects of Silver Island Films on the Luminescent Intensity and Decay Times of Lanthanide Chelates, Journal of Fluorescence, vol. 12, Nos. 3/4, 2002, pp. 431-437.*

* cited by examiner

Primary Examiner — Melanie J Yu
(74) Attorney, Agent, or Firm — Richard Aron Osman

(57) ABSTRACT

A lanthanide chelate is linked to a noble metal substrate at a proximity wherein the substrate enhances a fluorescent emission of the lanthanide by at least 20-fold when the chelate is illuminated at an excitation wavelength that induces a transition in the lanthanide that results in the fluorescent emission.

31 Claims, No Drawings

US 7,906,343 B2

SURFACE-ENHANCED LANTHANIDE CHELATES

CROSS-REFERENCE TO RELATED APPLICATION

Priority is claimed to U.S. provisional application No. 60/646,902 filed Jan. 24, 2005, incorporated herein by reference.

This work was supported by Federal Grant No. NIH 1 R21 AI055728-01. The U.S. government may have rights in any patent issuing on this application.

BACKGROUND OF THE INVENTION

The field of the invention is surface enhancement of lanthanide chelates and applications in biological detection assays.

Surface enhancement of fluorescence is one of several phenomena derived from excitation of surface plasmons in noble metal nanoparticles in the vicinity of analyte molecules [1-2]. The growing field of plasmonics has produced a number of new techniques of great value to biomedical optics including surface plasmon resonance spectroscopy (SPRS) for reporterless detection of binding events [3-4] and surface enhanced Raman spectroscopy (SERS), which offers extremely sensitive and molecularly selective detection of analytes [5-8].

In recent years, there have been numerous publications on the development of surface-enhanced fluorescence [e.g. 9-18], and a few groups have described surface enhancement of lanthanide emission [19-22]. A 5-fold increase in the emission of europium on silver island films has been demonstrated by Weitz et al. [19]. Surface enhanced luminescence from lanthanides has also been described by Hayakawa et al. in sol gels [20]. Lakowicz et al. achieved modest increases in the emission of europium and terbium sandwiched between silver island films [21]. Nabika and Deki obtained enhanced luminescence of europium in the presence of a colloidal dispersion of silver particles [22]. All of this work has involved lanthanide ions that already have good quantum efficiency (i.e., europium and terbium) and good optical absorption (i.e., the chelate studies used an antenna to absorb the excitation light for subsequent energy transfer to the lanthanide). In this case the surface enhancement possible on the emission side is limited because the quantum efficiency cannot exceed one and the absorption is already good. The only possibility for further emission enhancement in this case is when the transition is saturated (i.e., the finite radiative or decay rate limits the ability to re-excite the fluorophore), but fluorophore saturation is uncommon. We have shown that much larger enhancements are possible for lanthanides with lower quantum efficiency or low absorption coefficient, and that these larger enhancements in turn can be used to produce larger on/off ratios for proximity assays [37].

BRIEF SUMMARY OF THE INVENTION

One aspect of the invention is a lanthanide chelate comprising a lanthanide ion and a chelator chelating the lanthanide ion, wherein the chelate is linked to a noble metal substrate at a proximity wherein the substrate enhances a fluorescent emission of the lanthanide ion by at least 20-fold when the chelate is illuminated at an excitation wavelength that induces a transition in the lanthanide ion that results in the fluorescent emission, wherein (a) the chelator does not photosensitize the lanthanide ion, and/or (b) the transition has an un-enhanced quantum efficiency of less than 3%.

In specific embodiments, the substrate is a silver island film or a nanoparticle in a colloidal dispersion of noble metal nanoparticles.

In one embodiment, the lanthanide ion is terbium or europium and the chelator does not photosensitize the terbium. In other embodiments, the lanthanide ion is selected from the group consisting of selected from the group consisting of neodymium, holmium, erbium, praseodymium, samarium, dysprosium, thulium, and ytterbium.

In one embodiment, the chelate and substrate are linked together by a nucleic acid bound to the chelate and the substrate. In another embodiment, the chelate is bound to a first nucleic acid probe, the substrate is bound to a second nucleic acid probe, and the chelate and substrate are linked together by a target nucleic acid that is hybridized to the first and second nucleic acid probes.

Another aspect of the invention is a method for detecting fluorescent emission by a lanthanide ion, the method comprising the steps of: illuminating a lanthanide chelate at an excitation wavelength that induces a transition in the lanthanide ion resulting in fluorescent emission, said chelate comprising a lanthanide ion and a chelator chelating the lanthanide ion; and detecting the resultant fluorescent emission by the lanthanide ion; wherein the chelate is linked to a noble metal substrate at a proximity wherein the substrate enhances the fluorescent emission of the lanthanide ion by at least 20-fold, wherein (a) the chelator does not photosensitize the lanthanide ion, or (b) the transition has an un-enhanced quantum efficiency of less than 3%.

In one embodiment, the substrate is a nanoparticle in a colloidal dispersion of noble metal nanoparticles. In a further embodiment, the silver nanoparticle has a 50 nm diameter and the excitation wavelength is 488 nm.

In one embodiment, the lanthanide ion is selected from the group consisting of neodymium, holmium, erbium, praseodymium, samarium, dysprosium, thulium, and ytterbium.

The method may comprise the prior step of: contacting an analyte-containing sample with a first biomolecule bound to the substrate and a second biomolecule labeled with the chelate; wherein the first and second biomolecules specifically and non-competitively bind the analyte to form a bridge linking the substrate and chelate together at the proximity; wherein the resultant fluorescent emission is an indication of the presence of the analyte in the sample; and wherein background fluorescence from unlinked lanthanide chelate is less than 5% of the resultant fluorescent emission.

In another embodiment, the method comprises the prior step of: contacting an analyte-containing sample with a first biomolecule bound to the substrate and a second biomolecule labeled with the chelate; wherein the first and second biomolecules are antibodies that specifically and non-competitively bind the analyte to form a bridge linking the substrate and lanthanide chelate together at the proximity; wherein the resultant fluorescent emission by the lanthanide is an indication of the presence of the analyte in the sample; and wherein background fluorescence from unlinked lanthanide chelate is less than 5% of the resultant fluorescent emission.

In another embodiment, the method comprises the prior step of: contacting an analyte-containing sample with a first biomolecule bound to the substrate and a second biomolecule labeled with the chelate, wherein the analyte is a target nucleic acid, and the first and second biomolecules are nucleic acid probes that specifically and non-competitively hybridize to the target nucleic acid to form a bridge linking the substrate and chelate together at the proximity; wherein the resultant fluorescent emission by the lanthanide ion is an indication of the presence of the analyte in the sample; and wherein background fluorescence from unlinked lanthanide chelate is less than 5% of the resultant fluorescent emission.

A further aspect of the invention is a kit for detecting an analyte in a sample, the kit comprising: a first biomolecule bound to a noble metal substrate; and a second biomolecule labeled with a lanthanide chelate comprising a lanthanide ion and a chelator; wherein the first and second biomolecules specifically and non-competitively bind the analyte to form a bridge linking the substrate and lanthanide chelate together at a proximity wherein the substrate enhances a fluorescent emission of the lanthanide ion by at least 20-fold when the chelate is illuminated at an excitation wavelength that induces a transition in the lanthanide ion that results in the fluorescent emission, wherein (a) the chelator does not photosensitize the lanthanide ion, or (b) the transition has an un-enhanced quantum efficiency of less than 3%.

In one embodiment of the kit, the substrate is a silver nanoparticle of 50 nm diameter in a colloidal dispersion of silver nanoparticles. In another embodiment, the lanthanide ion is selected from the group consisting of neodymium, holmium, erbium, praseodymium, samarium, dysprosium, thulium, and ytterbium. In a specific embodiment, the first and second biomolecules are antibodies. In another embodiment, the analyte is a target nucleic acid, and the first and second biomolecules are nucleic acid probes that specifically hybridize to the target nucleic acid.

DETAILED DESCRIPTION OF THE INVENTION

The invention provides compositions and methods for enhancing the emission properties of lanthanides, which can be used to produce large on/off ratios for proximity assays. In one aspect, the subject composition is a lanthanide chelate comprising a lanthanide ion and a chelator chelating the lanthanide ion. The chelate is linked to a noble metal substrate at a proximity wherein the substrate enhances a fluorescent emission of the lanthanide ion by at least 20-fold when the chelate is illuminated at an excitation wavelength that induces a transition in the lanthanide ion resulting in fluorescent emission. In the absence of surface enhancement by the noble metal substrate, the lanthanide chelates of the subject compositions and methods are weak fluorophores either because (a) the chelator does not photosensitize the lanthanide ion at the excitation wavelength, and/or (b) the emitting transition has a low to moderate quantum efficiency (QE).

QE refers to the percentage of the number of photons emitted by the lanthanide relative to the total number of photons absorbed by the lanthanide chelate. A high QE is greater than about 10%, a moderate QE is about 0.5 to 10%, and a low QE is less than about 0.5%. In specific embodiments, a lanthanide chelate is used in which the emitting transition has a moderate to low QE in the absence of surface enhancement (i.e. the un-enhanced QE); preferably the un-enhanced QE is less than about 5%, preferably less than 3%, and more preferably less than 1%. The un-enhanced QE of a lanthanide chelate of the subject compositions and methods can be determined by eliminating the noble metal structures that provide the enhancement. For example, for enhancements on a solid substrate such as a silver island film, the unenhanced measurement is performed on the same type of substrate the silver island film is deposited on except without the silver islands. Deposition may be performed by drop coating, dipping, or spin coating. For enhancements on colloid nanoparticles, unenhanced values are obtained by using a second solution without the particles, or by using a very thick spacer on the metal particles to place the fluorophore or lumiphore outside the enhancement range of the particle. Methods for measurement of quantum efficiency are described in the literature [49-50 and references therein]. The amount of light absorbed at the excitation wavelength is determined by a measurement of the sample absorbance at a known concentration. Then, by performing a measurement of the input power and emitted power one can determine the quantum efficiency. The amount of emitted power is determined by comparison of the emitted power for the sample of interest with a standard, which can include a fluorophor or phosphor, Mie scattering, Rayleigh scattering, or Raman scattering. This method is simpler than the measurement of the absolute emitted power. If the standard and sample of interest emit at different wavelengths, then the spectral response of the detection system can be calibrated, which includes a spectrally-selective element such as a spectrometer or a filter and a detector such as a photodiode or a photomultiplier. One may alternatively measure the absolute power through absolute calibration of the detection system. Using an integrating sphere or the detection of the emitted light allow collection of light at all emission angles.

An excitation light absorbing chelator absorbs light at the excitation wavelength by itself, or by virtue of being linked to an "antenna" photosensitizer molecule, and transfers that energy to (i.e. photosensitizes) the lanthanide ion. Exemplary self-sensitized chelators include thenoyltrifluoroacetone (TTA); and 1-(2-naphthyl)-4,4,4-trifluoro-1,3-butanedionate (NTA). Exemplary non-absorbing chelators include [ [(carboxymethyl)imino]bis(ethylenenitrilo)]-tetra-acetic acid (DTPA); 1,4,7,10-tetraazacyclododecane N, N', N'', N'''-tetraacetic acid (DOTA), etc., which can be sensitized with an antenna molecule such as 7-amino-4-methyl-2-quinolinol (carbostyril-124); 7-amino-4-methyl-2-coumarin (coumarin 120); Biocytinamide (Sigma-Aldrich, Inc., St. Louis, Mo.); etc. In a particular embodiment, the chelate comprises a sensitized chelator and a chelated samarium ion. In another embodiment, the chelate comprises an unsensitized chelator and a chelated terbium ion. Exemplary sensitized and unsensitized lanthanide chelates of the subject methods and compositions and their respective excitation and emission wavelengths are shown in Table 1.

TABLE 1

| Lanthanide | Chelator | Photo-sensitizer | QE | Excitation Wavelength (nm) | Emission Wavelength (nm) |
|---|---|---|---|---|---|
| Samarium | DTPA or DOTA with antenna | Yes | Moderate | 340 | 645 |
| Terbium | DPTA or DOTA | No | High | 488 | 545 |
| Ytterbium | DPTA or DOTA | No | Moderate | 980 | 1050 |
| Praseodymium | DPTA or DOTA | No | Moderate | 488 | 600 |
| Neodymium | DPTA or DOTA | No | Moderate | 810 | 880 |
| Thulium | DPTA or DOTA | No | Moderate | 670 | 800 |
| Samarium | DPTA or DOTA | No | Moderate | 410 | 645 |
| Europium | DPTA or DOTA | No | High | 400 | 615 |
| Dysprosium | DPTA or DOTA | No | Moderate | 488 | 565 |

TABLE 1-continued

| Lanthanide | Chelator | Photo-sensitizer | QE | Excitation Wavelength (nm) | Emission Wavelength (nm) |
|---|---|---|---|---|---|
| Holmium | DPTA or DOTA | No | Low | 488 | 550 |
| Erbium | DPTA or DOTA | No | Low | 488 | 550 |
| Dysprosium | DPTA or DOTA with antenna | Yes | Moderate | 340 | 565 |
| Neodymium | DPTA or DOTA | No | Moderate | 800 | 1000 |
| Samarium | DTPA or DOTA | Yes | Moderate | 488 | 645 |

Examples of DTPA with an antenna are described in [42] and [44].

The lanthanide chelate is linked to a noble metal substrate that has nanoscale dimensions. Preferred noble metals are gold, silver, and platinum. Numerous suitable substrates for surface enhancement of fluorescence are known in the art such as metal island films, metal films over nanospheres, triangular nanoparticle arrays fabricated with nanosphere lithography, cylindrical nanoparticle arrays fabricated with electron-beam lithography, etc. [34]. In a preferred embodiment, the substrate is a nanoparticle, particularly a nanoparticle in a liquid dispersion medium (e.g. colloidal gold, colloidal silver, etc.). For greatest enhancement, the nanoparticle has a diameter of about 5 to 100 nm. Preferably the nanoparticle has an average diameter of about 20, 30, 40, 50, 60, 70, or 80 nm. In one embodiment the nanoparticle is colloidal silver with an average particle size of about 50 nm. These particles can be produced using aqueous reduction chemistry [45,48] or purchased, for example from Ted Pella, Inc. We have found that in addition to providing surface enhancement, 50 nm particles increase absorbance of lanthanide chelates at an excitation wavelength of 488 nm. Descriptions of the variation of the resonant wavelength for nanostructures with size scale are described in the literature [40,43].

In certain embodiments, the noble metal substrate is a surface-confined nanostructure having nanoscale features, such as bumps, peaks, etc of <100 nm, that provide a roughened surface. The metal may be attached to an underlying surface of glass, silica, plastic, etc. In one embodiment, the nanostructure is a silver island film, which can be prepared using various methods known in the art [e.g. 17, 23-25, 34]. In a particular embodiment, the lanthanide chelate is samarium (TTA)3 on a silica coated silver island film [37].

The lanthanide chelate and substrate are linked together at a proximity wherein the substrate enhances a fluorescent emission of the lanthanide when the chelate is illuminated at an excitation wavelength that induces a transition in the lanthanide ion that results in the fluorescent emission. The fluorescence is increased by at least 10-fold, and preferably at least 20-, 50-, or 100-fold over levels of fluorescence observed in the absence of surface enhancement. For colloid measurements, the negative control for determining the enhancement factor is the same solution without the colloid or a colloid with a very thick spacer layer. For surface measurements, the unenhanced measurements are performed on the same substrate without the metal nanoparticles or islands or with a very thick spacer layer.

One aspect of the invention is a method for detecting fluorescent emission by a lanthanide comprising the steps of: illuminating a lanthanide chelate at an excitation wavelength that induces a transition in the lanthanide ion resulting in fluorescent emission; and detecting the resultant fluorescent emission by the lanthanide ion. The lanthanide chelate is linked to a noble metal substrate a proximity wherein the substrate enhances the fluorescent emission of the lanthanide by at least 20-fold. A chelator is used that does not photosensitize the lanthanide ion at the excitation wavelength, and/or the emitting transition has a low to moderate un-enhanced QE, and preferably has a QE of less than 3%.

The proximity for optimum enhancement is where about 1 to 100 nm, and more typically about 3 to 20 nm, separate the lanthanide chelate and the noble metal substrate. The separation can be achieved using a variety of linking agents, such as a silica [38-39], dextran, agarose, polyethelene glycol [39], cetyltrimethylammonium bromide (CTAB) [46-47], polymers, thiol alkanes [40], and biomolecules such as protein (e.g. streptavidin [26], serum albumin [17], etc.) nucleic acid, or lipids.

A lanthanide chelate and metal substrate linked together by a nucleic acid molecule can be used to probe for the presence of a target nucleic acid (i.e. nucleic acid analyte) in a biological sample. In one variation, the nucleic acid is labeled at or near one end (i.e. 5' or 3') with the lanthanide chelate, and the substrate is bound at or near the opposite end. The 5' and 3' ends of the nucleic acid are complementary to and hybridize with each other such that they form a double-stranded stem, while the middle portion of the nucleic acid probe is complementary to the target nucleic acid, forming a single-stranded loop in the absence of target nucleic acid (i.e. a hairpin structure). In the hairpin configuration, the proximity of the lanthanide chelate and substrate is too close for surface enhancement. The target nucleic acid, when added, hybridizes to the single stranded portion of the probe, causing the 5' and 3' ends of the probe to separate from each other thereby creating a linear nucleic acid that links the substrate and lanthanide chelate together at a proximity wherein the substrate enhances the fluorescent emission of the lanthanide ion. Surface enhancement typically occurs between about 3 and 20 nm which corresponds to approximately 9 to 60 nucleotides.

In another variation of the nucleic acid probe, the lanthanide chelate and substrate are at a proximity that results in surface-enhanced fluorescence when the probe is in the hairpin configuration. In this embodiment, the 5' and 3' ends of the probe separate from each other as the target nucleic acid hybridizes to the complementary portion of the probe, creating a linear nucleic acid, the ends of which are too distant for the metal substrate to enhance fluorescence of the lanthanide chelate. Thus, a reduction in fluorescence indicates the presence of target nucleic acid in the sample.

In another embodiment of the invention, a first biomolecule is bound to the metal substrate, and a second biomolecule is labeled with the lanthanide chelate. In one embodiment, the biomolecules are specific binding partners, and bind to each other forming a bridge that links the substrate and lanthanide chelate together at the fluorescence-enhancing proximity. Exemplary specific binding partners include streptavidin/biotin, antigen/antibody, complementary strands of nucleic acid (where specific binding occurs in the way of hybridization of the complementary strands), receptor/ligand, enzyme/substrate, etc. In another embodiment, the first and second biomolecules each specifically and non-competitively bind an analyte in a sandwich-type format. When a sample containing the analyte is added to a mixture of the substrate-bound first biomolecule and lanthanide chelate-labeled second biomolecule, the analyte binds the biomolecules, bridging them together and bringing the metal substrate and lanthanide chelate together at a proximity wherein the substrate enhances the fluorescent emission of the lanthanide ion, preferably at least 20-fold, upon illumination of the chelate at an excitation wavelength. Resultant fluorescent emission by the lanthanide ion is an indication of the presence of the analyte in the sample. Examples of first biomolecule/analyte/ second biomolecule combinations include: antibody/antigen/ antibody, probe nucleic acid/target nucleic acid/probe nucleic acid, enzyme/substrate/antibody, receptor/ligand/antibody, etc. Biomolecules can be labeled with lanthanide chelates using known methods including use of thiol-reactive [e.g. 27, 28] or amine-reactive [e.g. 29] linkers. In a particular embodiment, one antibody is bound to a lanthanide chelate (e.g. thulium, etc.), and a second antibody is bound to a noble metal substrate (e.g. silver, etc.), when the antibodies specifically bind an antigen (e.g. influenza virus hemagglutinin, etc.), proximity between the chelate and substrate leads to an enhancement of the luminescent signal of 100 times or more.

The sample can be any liquid substance containing or suspected of containing the analyte to be detected. For example, the sample may be a water or food sample being tested for contamination (e.g. by parasites, bacteria, industrial contaminants, etc.). In specific embodiments, the sample is a patient sample (e.g. blood, serum, saliva, urine, etc.). Examples of analytes routinely tested in patient samples are hormones (e.g. human chorionic gonadotropin (HCG)), tumor markers (e.g. prostate-specific antigen), viruses (e.g. HIV), etc. In a specific embodiment of the invention, the analyte is a Category A, B, or C agent as categorized by the U.S. Department of Health and Human Services Centers for Disease Control (CDC), such as: *Bacillus anthracis*, *Clostridium botulinum* toxin, *Yersinia pestis*, Smallpox (variola major), Tularemia (*Francisella tularensis*), Viral hemorrhagic fevers (filoviruses [e.g., Ebola, Marburg] and arenaviruses [e.g., Lassa, Machupo]), Brucellosis (*Brucella* species), Epsilon toxin of *Clostridium perfringens, Salmonella* species, *Escherichia coli* O157:H7, *Shigella*, Glanders (*Burkholderia mallei*), Melioidosis (*Burkholderia pseudomallei*), Psittacosis (*Chlamydia psittaci*), Q fever (*Coxiella burnetii*), Ricin toxin from *Ricinus communis* (castor beans), *Staphylococcal* enterotoxin B, Typhus fever (*Rickettsia prowazekii*), Viral encephalitis (alphaviruses [e.g., Venezuelan equine encephalitis, eastern equine encephalitis, western equine encephalitis]), *Vibrio cholerae, Cryptosporidium parvum, Vibrio cholerae*, and *Cryptosporidium parvum*. In a preferred embodiment, the CDC category A, B, or C agent is detected in a homogeneous assay without a washing step, as described below.

When used for analyte detection, the lanthanide chelates of the invention preferably have minimal detectable fluorescence in the absence of surface enhancement (i.e. background fluorescence is minimal). Preferably background fluorescence, which results from free lanthanide chelate that does not linked to the substrate via the analyte, accounts for less than 5%, preferably less than 3%, and more preferably less than 1% of total fluorescence detected. In a preferred embodiment, the lanthanide chelate has no detectable fluorescence in the absence of surface-enhancement. If the noble metal substrate is a nanoparticle in a colloidal dispersion of noble metal nanoparticles, a homogeneous assay can be performed where all reactants are in suspension and no washing steps are required to remove lanthanide chelates that have not bound to the analyte. Thus, in a particular embodiment of the subject method, the metal substrate is a nanoparticle in a colloidal dispersion of noble metal particles, the method is performed without a washing step, and the detection step is performed without gating out background fluorescence (e.g. as in time-resolved fluorescence). Typical concentrations of colloid are around $10^{10}$ particles/ml, typical sample volumes are 10-100 microliters, typical incubation times are around 10 minutes to 1 hour, at a typical temperature of between 25 and 37° C.; room temperature is preferred for simplicity.

The excitation and detection steps of the subject methods can be performed using conventional light sources (e.g. Nd:YAG pumped dye laser, diode laser, nitrogen laser, light emitting diode, or filtered lamp) and fluorimeters. A preferred excitation source would be a laser diode, LED, or filtered lamp. Detection can be performed using a fluorimeter, filtered solid state detectors [such as a silicon photodiode or avalanche photodiode (APD)] or photomultiplier tube (PMT), or a spectrometer with a solid state detector, PMT, or solid state array detector [such as a photodiode array or charge coupled device (CCD)]. A preferred detection system is a filtered solid state detector or a compact spectrometers using an array detector.

A further aspect of the invention is a kit for detecting an analyte in a sample, the kit comprising: a first biomolecule bound to a noble metal substrate; and a second biomolecule labeled with a lanthanide chelate comprising a lanthanide ion and a chelator, wherein the first and second biomolecules specifically and non-competitively bind the analyte to form a bridge linking the substrate and lanthanide chelate together at a proximity wherein the substrate enhances a fluorescent emission of the lanthanide ion by at least 20-fold when the chelate is illuminated at an excitation wavelength that induces a transition in the lanthanide ion that results in the fluorescent emission, wherein (a) the chelator does not photosensitize the lanthanide ion, and/or (b) the emitting transition has a low un-enhanced quantum efficiency, and preferably a quantum efficiency of less than 3%. In one embodiment, the substrate is a silver nanoparticle of 50 nm diameter in a colloidal dispersion of silver nanoparticles. In another embodiment the lanthanide ion is terbium or europium, and the chelator does not photosensitize the terbium ion. In another embodiment, the lanthanide ion is selected from the group consisting of neodymium, holmium, erbium, praseodymium, samarium, dysprosium, thulium, and ytterbium. In a specific embodiment, the first and second biomolecules are antibodies. In another embodiment, the analyte is a target nucleic acid, and the first and second biomolecules are nucleic acid probes that specifically hybridize to the target nucleic acid.

EXAMPLE 1

Homogeneous Assays for Detection of Influenza Virus Hemagglutinin

We describe here approaches to detection using the influenza virus as an example of our surface-enhanced lanthanide chelate assay. Of course our assay can be as readily applied to detecting biological particles from agents other than influenza. Methods of producing suitable high affinity, non-competitive antibodies to a wide variety of target agents are well-known to those skilled in the art, as are methods for making suitable antibody fragments.

Conjugation of Reporters to Antibodies. Protocols for attaching gold particles to antibodies are well known in the art [35]. Analogous procedures are available for attaching silver particles [36]. Alternatively, silver can be deposited onto gold particles already attached to the protein, e.g. wherein the gold catalyzes the reduction of Ag+ by hydroquinone.

A variety of chelates modified for protein conjugation are commercially available. For example, Macrocyclics (Dallas, Tex.) sells bifunctional ligands suitable for lanthanides including tetraazacyclododecane-1,4,7,10-tetraacetic acid (DOTA) or Diethylenetriaminepentaacetic acid (DTPA). These ligands have a reactive site such as NHS-ester, which reacts with amine groups. Chelates modified with an aromatic isothiocyanate group readily react with free amino groups on the protein forming stable thiourea bonds.

Hemagglutinin protein assay. A lanthanide chelate modified with an aromatic isothiocyanate group is conjugated to one of two non-competitive anti-HA antibodies (see, e.g. refs. 30, 31) using conventional protocols (supra), under mild reaction conditions. Several chelates may be conjugated to each antibody. The second anti-HA antibody is conjugated to gold nanoparticles following an established protocol [32]. Silver is then deposited onto the gold nanoparticles using hydroquinone. In an alternative embodiment, the silver particles are coated with silica using (3-aminopropyl)triethoxysilane (APS) and tetraethyl orthosilicate (TEOS) and the amine groups used for conjugation to the antibody using linker arms.

To test the complexes, a solution of equal amounts of the two types of labeled anti-HA antibodies are excited at the excitation wavelength(s) for the lanthanide ion of the reporter, and the expected emission wavelength is monitored to obtain a baseline. When the HA is introduced to the solution and quickly stirred, the signal increases as the sandwich complexes form.

Various alternative approaches may be used. Streptavidin biotin complexes may be used as spacers or other tethers such as polyethylene glycol may be used to vary the spacing between the antibody and the silver particle or the lanthanide chelate.

Nucleoprotein antibodies may be used to detect influenza instead of the anti-HA antibodies.

Alternative Assays. Other types of assays can also be performed using surface enhanced emission. For example, a sandwich assay can be performed on a silver island film. In this case one antibody is attached to the silver film, and the second antibody is attached to the lanthanide chelate. In the presence of the target, a sandwich is formed between the antibody on the silver surface, the target, and the lanthanide chelate antibody. This sandwich produces enhanced emission from the lanthanide chelate. Washing steps performed between applications of each layer of the sandwich can be used to increase the assay detection limits.

A third type of assay is based on agglutination. As for the homogenous assay, antibodies are attached to silver colloid particles and to lanthanide chelates. In the presence of target molecules, the silver colloid and lanthanide chelates agglutinate. The close interaction of the agglutinated silver particles and lanthanide chelates provides surface enhancement of the lanthanide chelate. An additional advantage of the agglutination assay is that the presence of many silver particles close together can lead to the formation of hot spots that create increase the surface enhancement effect.

EXAMPLE 2

Surface Enhancement of Unsensitized Terbium Chelates and Sensitized Samarium Chelates We prepared silica coated silver island films using well established protocols [43]. We examined the effect of surface enhancement on samarium (Sm) chelated with thenoyltrifluoroacetone (TTA) by applying the chelate to the silver island film by drop coating. The sample was excited at 340 nm using a fluorimeter. Detection was performed at 645 nm. An enhancement of a factor of 10 to 100 was observed.

We have also examined surface enhancement of unsensitized terbium (Tb). Silver colloid with an average diameter of about 50 nm were prepared using the citrate method [45, 48]. The particles were subsequently coated with biotinylated BSA (bovine serum albumin) followed by streptavidin. The protein provides the required spacer between the metal surface and the lanthanide chelate, in this case, TbDTPA biocytinamide. Excitation was performed using an argon ion laser at 488 nm. Emission was detected at 545 nm with a spectrometer and a photomultiplier tube. We achieved an enhancement factor of two orders of magnitude.

EXAMPLE 3

Homogeneous Assay for Detection of HIV

Enhancement by silver island films can be exploited for assays [18] but for homogeneous proximity assays, colloids are more attractive. Silver colloids with an average diameter of about 50 nm are prepared using the well-known citrate method [45,48]. The particles are subsequently coated with a first antibody for the HIV-1 major core polypeptide, p24 [33]. Praseodymium DTPA biocytinamide is conjugated to a second antibody that binds p24 non-competitively with the first antibody. A sample 50-500 microliters containing HIV viral lysate is added to a reaction well containing the first and second antibodies. Specific binding of the antibodies to the p24 antigen provides the required spacer (approx. 10 nm) between the metal colloid and the lanthanide chelate. The sample is excited at 488 nm and fluorescent emission detected at 600 nm indicates presence of antibody-bound p24 antigen.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. As used herein, the singular forms "a," "an," and "the," refer to both the singular as well as plural, unless the context clearly indicates otherwise.

REFERENCES

1. J. R. Lakowicz, Anal. Biochem. (2001) 298:1-24
2. P. J. Tarcha et al, Appl. Spectrosc. (1999) 53:43-48
3. A. J. Haes et al, J. Am. Chem. Soc. (2005) 127:2264-71
4. A. D. McFarland and R. P. V. Duyne, Nano Lett. (2003) 3:1057-1062
5. C. L. Haynes et al, J. Raman Spectrosc. (2005) 36:471-484
6. A. M. Michaels et al, J. Phys. Chem. (2000) 104:11965-11971
7. Y. C. Cao et al, Science (2002) 297:1536-1540
8. S. Nie and S. R. Emory, Science (1997) 275:1102-6
9. K. Aslan et al, Current Opinion in Biotechnology (2005) 16:55-62
10. J. R. Lakowicz et al, J. of Fluorescence (2004) 14:425-441
11. E. Matveeva et al, Analytical Biochemistry (2004) 334:303-311
12. M. Wu et al, F. of Fluorescence (2005) 15:54-59
13. K. Aslan et al, Current Opinion in Chemical Biology (2005) 9:538-544

14. E. Matveeva et al, J. of Immunological Methods (2005) 302:26-35
15. J. R. Lakowicz, U.S. Patent Application Pub. No. U.S. 2002/0160400
16. I. Gryczynski et al, J. of Fluorescence (2002) 12:11-13
17. K. Aslan et al, J. of Fluorescence (2005) 15:643-654
18. E. Matveeva et al, Proc SPIE (2004) 5327:45-52
19. D. A. Weitz et al., Optics Letters (1982) 7:89-91.
20. T. Hayakawa et al., Applied Physics Letters (1999) 74:1513-1515.
21. J. R. Lakowicz et al, J. of Fluorescence (2002) 12:431-437.
22. H. Nabika and S. Deki, The European Physical Journal D—Atomic, Molecular and Optical Physics (2003) 24:369-372.
23. P. He et al, Langmuir (2004) 20:10260-7.
24. H. Li and B. M. Cullum, Appl Spectrosc. (2005) 59:410-7.
25. L. Bao et al., Anal Chem. (2004) 76:4531-6.
26. J. R. Lakowicz et al, Proc. SPIE (2004) 5327:10-28.
27. P. Ge et al, Bioconjug Chem. (2003) 14:870-876
28. J. Chen et al, Bioconjug Chem. (1999) 10:311-315
29. M. Li et al, Bioconjug Chem. (1997) 8:127-132
30. M. D. Lubeck and W. Gerhard, Virology (1981) 113:64-72
31. A. J. Caton et al, Cell (1982) 31:417-427
32. J. Beesley, "Colloidal gold. A new perspective for cytochemical marking," in *Royal Microscopical Society Handbook* (Oxford Science Publications, 1989), Vol. 17.
33. S. Kontio, J Immunol Methods. (1991) 139:257-63
34. C. L. Haynes et al, Anal. Chem. (2005) 77:338A-346A.
35. S. E. Coleman et al, Infect Immun. (1990) 58:332-40.
36. S. Schultz et al, Proc Natl Acad Sci U S A. (2000) 97:996-1001.
37. J. P. Haushalter et al, Proc. SPIE (2005) 5703:42-49.
38. S. P. Mulvaney et al., Langmuir (2003) 19:4784-4790.
39. J. Hampl et al., Anal. Biochem. (2001) 288:176-187.
40. C. L. Haynes et al., J. Phys. Chem. B (2003) 107:7426-7433.
41. O. Lyandres et al., Anal. Chem. (2005) 77:6134-9.
42. S. Quici et al., Inorg. Chem. (2005) 44:529-537.
43. R. Gupta et al., J. Appl. Phys. (2002) 92:5264-5271.
44. M. Li et al., Bioconjug. Chem. (1997) 8:127-132
45. S. Liu et al., Anal. Chem. (2005) 77:2595-600.
46. H. Wang et al., J. Am. Chem. Soc. (2005) 127:14992-14993.
47. Z. M. Sui et al., Chem. Lett. (2005) 34:100-101.
48. P. C., Lee, and D. Meisel, J. Phys. Chem. (1982) 86:3391-3395
49. Y. Haas and G. Stein, J. Phys. Chem. (1971) 75:3668-3677.
50. W. R. Dawson and J. L. Kropp, J. Opt. Soc. Am. (1965) 55:822-828.

What is claimed is:

1. A lanthanide chelate comprising a lanthanide ion and a chelator chelating the lanthanide ion, wherein the chelate is linked to a noble metal substrate at a proximity wherein the substrate enhances a fluorescent emission of the lanthanide ion by at least 20-fold when the chelate is illuminated at an excitation wavelength that induces a transition in the lanthanide ion that results in the fluorescent emission, wherein (a) the chelator does not photosensitize the lanthanide ion, and/or (b) the transition has an un-enhanced quantum efficiency of less than 3%.

2. The chelate of claim 1 wherein the substrate is in a silver island film.

3. The chelate of claim 1 wherein the substrate is a nanoparticle in a colloidal dispersion of noble metal nanoparticles.

4. The chelate of claim 1 wherein the substrate is a 50nm silver nanoparticle in a colloidal dispersion of silver nanoparticles.

5. The chelate of claim 1 wherein the chelator does not photosensitize the lanthanide ion, and the lanthanide ion is terbium.

6. The chelate of claim 1 wherein the lanthanide ion is selected from the group consisting of selected from the group consisting of neodymium, holmium, erbium, praseodymium, samarium, dysprosium, thulium, and ytterbium.

7. The chelate of claim 1 wherein the chelate and substrate are linked together by a nucleic acid bound to the chelate and the substrate.

8. The chelate of claim 1 wherein the chelate is bound to a first nucleic acid probe, the substrate is bound to a second nucleic acid probe, and the chelate and substrate are linked together by a target nucleic acid that is hybridized to the first and second nucleic acid probes.

9. A method for detecting fluorescent emission by a lanthanide ion, the method comprising the steps of:
    illuminating a lanthanide chelate at an excitation wavelength that induces a transition in the lanthanide ion resulting in fluorescent emission, said chelate comprising a lanthanide ion and a chelator chelating the lanthanide ion; and
    detecting the resultant fluorescent emission by the lanthanide ion;
    wherein the chelate is linked to a noble metal substrate at a proximity wherein the substrate enhances the fluorescent emission of the lanthanide ion by at least 20-fold, wherein (a) the chelator does not photosensitize the lanthanide ion, and/or (b) the transition has an un-enhanced quantum efficiency of less than 3%.

10. The method of claim 9 wherein the substrate is a nanoparticle in a colloidal dispersion of noble metal nanoparticles.

11. The method of claim 9 wherein the substrate is a silver nanoparticle of 50nm diameter and the excitation wavelength is 488nm.

12. The method of claim 9 wherein the lanthanide ion is selected from the group consisting of neodymium, holmium, erbium, praseodymium, samarium, dysprosium, thulium, and ytterbium.

13. The method of claim 9 comprising the prior step of:
    contacting an analyte-containing sample with a first biomolecule bound to the substrate and a second biomolecule labeled with the chelate;
    wherein the first and second biomolecules specifically and non-competitively bind the analyte to form a bridge linking the substrate and chelate together at the proximity; wherein the resultant fluorescent emission is an indication of the presence of the analyte in the sample; and
    wherein background fluorescence from unlinked lanthanide chelate is less than 5% of the resultant fluorescent emission.

14. The method of claim 9 comprising the prior step of:
    contacting an analyte-containing sample with a first biomolecule bound to the substrate and a second biomolecule labeled with the chelate;
    wherein the first and second biomolecules are antibodies that specifically and non-competitively bind the analyte to form a bridge linking the substrate and lanthanide chelate together at the proximity; wherein the resultant fluorescent emission by the lanthanide is an indication of the presence of the analyte in the sample; and wherein background fluorescence is less than 5% of the resultant fluorescent emission.

15. The method of claim 9 comprising the prior step of:
contacting an analyte-containing sample with a first biomolecule bound to the substrate and a second biomolecule labeled with the chelate,
wherein the analyte is a target nucleic acid, and the first and second biomolecules are nucleic acid probes that specifically and non-competitively hybridize to the target nucleic acid to form a bridge linking the substrate and chelate together at the proximity; wherein the resultant fluorescent emission by the lanthanide ion is an indication of the presence of the analyte in the sample; and wherein background fluorescence of the unbound lanthanide is less than 5% of the resultant fluorescent emission.

16. A kit for detecting an analyte in a sample, the kit comprising:
a first biomolecule bound to a noble metal substrate; and
a second biomolecule labeled with a lanthanide chelate comprising a lanthanide ion and a chelator;
wherein the first and second biomolecules specifically and non-competitively bind the analyte to form a bridge linking the substrate and lanthanide chelate together at a proximity wherein the substrate enhances a fluorescent emission of the lanthanide ion by at least 20-fold when the chelate is illuminated at an excitation wavelength that induces a transition in the lanthanide ion that results in the fluorescent emission, wherein (a) the chelator does not photosensitize the lanthanide ion, and/or (b) the transition has an un-enhanced quantum efficiency of less than 3%.

17. The kit of claim 16 wherein the substrate is a silver nanoparticle of 50nm diameter in a colloidal dispersion of silver nanoparticles.

18. The kit of claim 16 wherein the lanthanide ion is selected from the group consisting of neodymium, holmium, erbium, praseodymium, samarium, dysprosium, thulium, and ytterbium.

19. The kit of claim 16 wherein the first and second biomolecules are antibodies.

20. The kit of claim 16 wherein the analyte is a target nucleic acid, and the first and second biomolecules are nucleic acid probes that specifically hybridize to the target nucleic acid.

21. The method of claim 9 wherein the substrate is in a silver island film.

22. The method of claim 9 wherein the chelator does not photosensitize the lanthanide ion, and the lanthandide ion is terbium or europium.

23. The method of claim 9 wherein the lanthanide ion is selected from the group consisting of selected from the group consisting of neodymium, holmium, and erbium.

24. The method of claim 9 wherein the lanthanide chelate has no detectable fluorescence in the absence of surface-enhancement.

25. The method of claim 9 wherein the metal substrate is a nanoparticle in a colloidal dispersion of noble metal particles, the method is performed without a washing step, and the detection step is performed without gating out background fluorescence.

26. The method of claim 9 wherein wherein the lanthanide ion is samarium and the chelator is thenoyltrifluoroacetone (TTA) and a silver island film comprises the substrate.

27. The method of claim 9 wherein the lanthanide ion is terbium and the chelator is TbDTPA biocytinamide, and the substrate is a 50nm silver nanoparticle in a colloidal dispersion of silver nanoparticles.

28. The method of claim 9 wherein the chelator is [(carboxymethyl)iminol]bis(ethylenenitrilo)]-tetra-acetic acid (DTPA) or 1,4,7,10- tetraazacyclododecane N, N', N", N"'-tetraacetic acid (DOTA).

29. The chelate of claim 1 wherein (a) the chelator does not photosensitize the lanthanide ion, and (b) the transition has an un-enhanced quantum efficiency of less than 3%.

30. The method of claim 9 wherein (a) the chelator does not photosensitize the lanthanide ion, and (b) the transition has an un-enhanced quantum efficiency of less than 3%.

31. The kit of claim 16 wherein (a) the chelator does not photosensitize the lanthanide ion, and (b) the transition has an un-enhanced quantum efficiency of less than 3%.

* * * * *